United States Patent [19]

Umezawa et al.

[11] Patent Number: 4,556,735
[45] Date of Patent: Dec. 3, 1985

[54] SPERGUALIN-RELATED COMPOUNDS HAVING A PHENYLENE GROUP AS WELL AS A PROCESS FOR PRODUCING THE SAME

[75] Inventors: Hamao Umezawa; Tomio Takeuchi; Rinzo Nishizawa; Katsutoshi Takahashi, all of Tokyo; Teruya Nakamura, Kusatsu; Yoshihisa Umeda, Otsu, all of Japan

[73] Assignee: Zaidan Hojin Biseibutsu Kagaku Kenkyukai, Tokyo, Japan

[21] Appl. No.: 706,312

[22] Filed: Feb. 27, 1985

[30] Foreign Application Priority Data

Mar. 2, 1984 [JP] Japan ................. 59-38615

[51] Int. Cl.$^4$ ............................ C07C 103/28
[52] U.S. Cl. ................................. 564/157
[58] Field of Search ........................ 564/157

[56] References Cited

U.S. PATENT DOCUMENTS 4,416,899 11/1983 Umezawa et al. ............... 514/626
4,430,346 2/1984 Umezawa et al. ............... 514/546

FOREIGN PATENT DOCUMENTS 2111480 7/1983 United Kingdom .

OTHER PUBLICATIONS

Umezawa, et al., Journal of Antibiotics, vol. 34, pp. 1619–1627.

*Primary Examiner*—Charles F. Warren
*Assistant Examiner*—Carolyn S. Greason
*Attorney, Agent, or Firm*—Henry C. Nields

[57] ABSTRACT

The invention relates to Spergualin-related compounds of the formula:

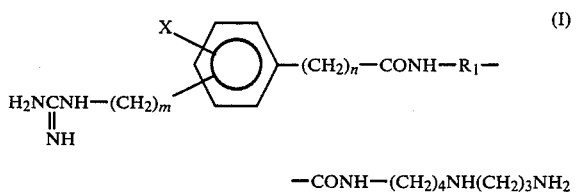

(wherein $R_1$ is a lower alkylene group which may be substituted by a hydroxymethyl group; X is a hydrogen atom or a halogen atom; m and n are each 0 or an integer of 1 to 5) and salts thereof and a process for producing the same.

5 Claims, 1 Drawing Figure

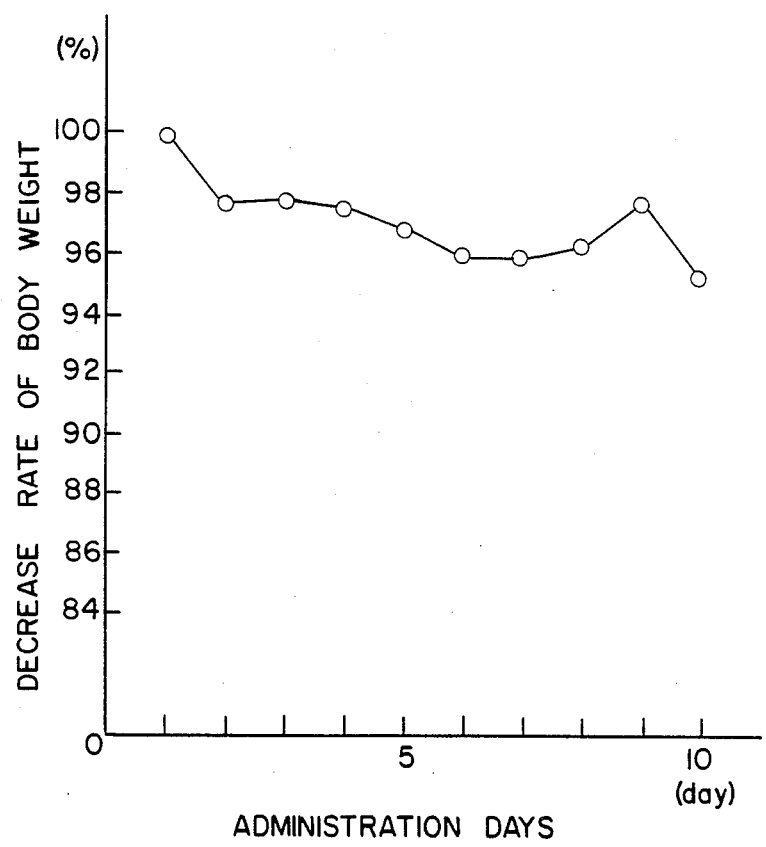

SPERGUALIN-RELATED COMPOUNDS HAVING A PHENYLENE GROUP AS WELL AS A PROCESS FOR PRODUCING THE SAME

BACKGROUND OF THE INVENTION

1. Field of the Invention

The present invention relates to novel Spergualin-related compounds, and a process for producing the same. More particularly, the invention relates to Spergualin-related compounds of the formula:

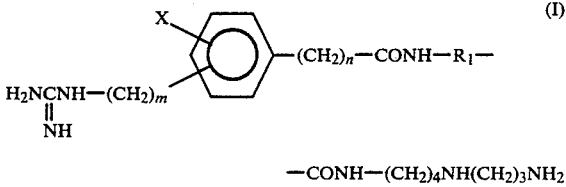
—CONH—(CH$_2$)$_4$NH(CH$_2$)$_3$NH$_2$ (I)

(wherein R$_1$ is a lower alkylene group which may be substituted by a hydroxymethyl group; X is a hydrogen atom or a halogen atom; m and n are each 0 or an integer of 1 to 5) and salts thereof, as well as a process for producing phenylene group containing Spergualin-related compounds of formula (I) and salts thereof characterized by removing the protecting groups from a protected Spergualin-related compound of the formula:

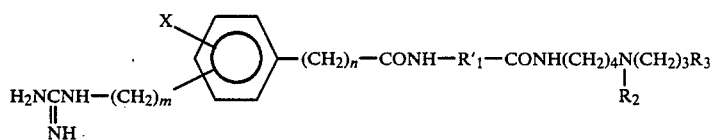

(wherein R'$_1$ is a lower alkylene group which may be substituted by a hydroxymethyl group, the hydroxyl group of which may be protected; R$_2$ is an amino protecting group; R$_3$ is a protected amino group; X, m and n are the same as defined above).

2. Description of the Prior Art

Spergualin is a compound that was isolated from a culture filtrate of a Spergualin producing microorganism of the genus Bacillus by Umezawa, one of the inventors of the present invention, and others. Spergualin has the following structure:

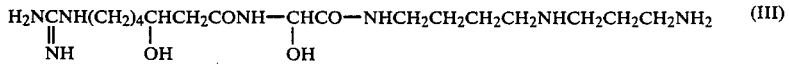

Spergualin has the ability to inhibit the growth of Gram-positive and Gram-negative microorganisms. It has been proved to have significant antineoplastic effects on experiments on the curing of mouse leukemia L1210, leukemia EL-4, and Ehrlich carcinoma, Sarcoma 180. For these reasons, Spergualin is considered to be a promising antineoplastic agent [see Japanese Patent Kokai (Laid-open) No. 48957/1982].

Umezawa et al. also found that Spergualin derivatives such as acylated compounds at 15-position have similar effects [Japanese Patent Kokai (Laid-open) Nos. 185254/1982 and 62152/1983].

However, Spergualin and its known derivatives are unstable in an aqueous solution.

SUMMARY OF THE INVENTION

Therefore, the present inventors conducted various studies to find Spergualin-related compounds which are stable and retain high activity in aqueous solutions. As a result, the inventors have found that the compounds of formula (I) have a higher stability and activity, and this finding has led to the accomplishment of the present invention.

REFERENCE TO THE DRAWING

The drawing depicts the relationship between the decrease rate of body weight of rats and the days of administering the compound of the present invention for the toxicity test of the compounds.

DETAILED DESCRIPTION OF THE INVENTION

The compounds of the present invention have a superior antitumor activity, a relatively low toxicity and a superior stability of the compounds in an aqueous solution which is very important for the formulation in an aqueous form such as injection and hence are considered to be promising as medicines such as antitumor agents.

The Spergualin-related compounds of formula (I) of the present invention are hereunder described in detail:
R$_1$ is a lower alkylene group which may have a hydroxymethyl group as a substituent, and illustrative examples are methylene, ethylene, propylene, hydroxymethylmethylene, 1-hydroxymethylethylene, 2-hydroxymethylethylene, 1,2-di(hydroxymethyl)ethylene, 1-hydroxymethylpropylene, 2-hydroxymethylpropylene, 3-hydroxymethylpropylene, 1,2-di(hydroxymethyl)propylene, 1,3-di(hydroxymethyl)propylene, 2,3-di(hydroxymethyl)propylene, and 1,2,3-tri(hydroxymethyl)propylene; X is a hydrogen atom or a halogen atom such as chlorine, bromine, fluorine or iodine; m or n is 0 or an integer of 1 to 5; the methylene groups in formula (I) may assume the ortho-, meta- or para-position with respect to each other.

Specific examples of the Spergualin-related compound of formula (I) are listed below, wherein GP, GMP, GPro and TAD are the abbreviations for "guanidinophenyl", "guanidinomethylphenyl", "guanidinopropyl" and "triazadecane", respectively:

10-{N-[4-(3-GP)Butanoyl]glycyl}-1,5,10-TAD
10-{N-[4-(3-GP)Butanoyl]-L-seryl}-1,5,10-TAD
10-{N-[4-(4-GP)Butanoyl]glycyl}-1,5,10-TAD
10-{N-[4-(4-GP)Butanoyl]-L-seryl}-1,5,10-TAD
10-{N-[4-(4-GP)Butanoyl]-β-aranyl}-1,5,10-TAD
10-{N-[4-(4-GP)Butanoyl]-γ-aminobutanoyl}-1,5,10-TAD
10-{N-[4-(2-Chloro-4-GP)butanoyl]glycyl}-1,5,10-TAD 10-{N-[4-(2-Chloro-4-GP)butanoyl]-L-seryl}-1,5,10-TAD
10-{N-[4-(2-Chloro-4-GP)butanoyl]-β-alanyl}-1,5,10-TAD
10-{N-[4-(2-Chloro-4-GP)butanoyl]-γ-aminobutanoyl}1,5,10-TAD
10-{N-[4-(3-Chloro-4-GP)butanoyl]glycyl}-1,5,10-TAD
10-{N-[4-(3-Chloro-4-GP)butanoyl]-L-seryl}-1,5,10-TAD
10-{N-[4-(3-Chloro-4-GP)butanoyl]-β-alanyl}-1,5,10-TAD
10-{N-[4-(3-Chloro-4-GP)butanoyl]-γ-aminobutanoyl}1,5,10-TAD
10-{N-[3-(2-Fluoro-4-GP)butanoyl]glycyl}-1,5,10-TAD
10-{N-[4-(2-Fluoro-4-GP)butanoyl]-L-seryl}-1,5,10-TAD
10-{N-[4-(3-Fluoro-4-GP)butanoyl]glycyl}-1,5,10-TAD
10-{N-[4-(3-Fluoro-4-GP)butanoyl]-L-seryl}-1,5,10-TAD
10-{N-[5-(3-GP)Pentanoyl]glycyl}-1,5,10-TAD
10-{N-[5-(3-GP)Pentanoyl]-L-seryl}-1,5,10-TAD
10-{N-[5-(4-GP)Pentanoyl]glycyl}-1,5,10-TAD
10-{N-[5-(4-GP)Pentanoyl]-L-seryl}-1,5,10-TAD
10-{N-[5-(2-Chloro-4-GP)pentanoyl]glycyl}-1,5,10-TAD
10-{N-[5-(2-Chloro-4-GP)pentanoyl]-L-seryl}-1,5,10-TAD
10-{N-[5-(3-Chloro-4-GP)pentanoyl]glycyl}-1,5,10-TAD
10-{N-[5-(3-Chloro-4-GP)pentanoyl]-L-seryl}-1,5,10-TAD
10-{N-[6-(4-GP)Hexanoyl]glycyl}-1,5,10-TAD
10-{N-[6-(4-GP)Hexanoyl]-L-seryl}-1,5,10-TAD
10-{N-[6-(2-Chloro-4-GP)hexanoyl]glycyl}-1,5,10-TAD
10-{N-[6-(2-Chloro-4-GP)hexanoyl]-L-seryl}-1,5,10-TAD
10-{N-[6-(3-Chloro-4-GP)hexanoyl]glycyl}-1,5,10-TAD
10-{N-[6-(3-Chloro-4-GP)hexanoyl]-L-seryl}-1,5,10-TAD
10-{N-[3-(3-GMP)Propanoyl]glycyl}-1,5,10-TAD
10-{N-[3-(3-GMP)Propanoyl]-L-seryl}-1,5,10-TAD
10-{N-[3-(4-GMP)Propanoyl]glycyl}-1,5,10-TAD
10-{N-[3-(4-GMP)Propanoyl]-L-seryl}-1,5,10-TAD
10-{N-[3-(2-Chloro-4-GMP)propanoyl]glycyl}-1,5,10-TAD
10-{N-[3-(2-Chloro-4-GMP)propanoyl]-L-seryl}-1,5,10-TAD
10-{N-[3-(3-Chloro-4-GMP)propanoyl]glycyl}-1,5,10-TAD
10-{N-[3-(3-Chloro-4-GMP)propanoyl]-L-seryl}-1,5,10-TAD
10-{N-[4-(4-GMP)Butanoyl]glycyl}-1,5,10-TAD
10-{N-[4-(4-GMP)Butanoyl]-L-ceryl}-1,5,10-TAD
10-{N-[4-(2-Chloro-4-GMP)butanoyl]glycyl}-1,5,10-TAD
10-{N-[4-(2-Chloro-4-GMP)butanoyl]-L-seryl}-1,5,10-TAD
10-{N-[4-(3-Chloro-4-GMP)butanoyl]glycyl}-1,5,10-TAD
10-{N-[4-(3-Chloro-4-GMP)butanoyl]-L-seryl}-1,5,10-TAD
10-{N-[5-(2-GMP)Pentanoyl]glycyl}-1,5,10-TAD
10-{N-[5-(2-GMP)Pentanoyl]-L-seryl}-1,5,10-TAD
10-{N-[5-(4-GMP)Pentanoyl]glycyl}-1,5,10-TAD
10-{N-[5-(4-GMP)Pentanoyl]-L-seryl}-1,5,10-TAD
10-{N-[5-(2-Chloro-4-GMP)pentanoyl]glycyl}-1,5,10-TAD
10-{N-[5-(2-Chloro-4-GMP)pentanoyl]-L-seryl}-1,5,10-TAD
10-{N-[5-(3-Chloro-4-GMP)pentanoyl]glycyl}-1,5,10-TAD
10-{N-[5-(3-Chloro-4-GMP)pentanoyl]-L-seryl}-1,5,10-TAD
10-{N-[3-(3-GPro)Benzoyl]glycyl}-1,5,10-TAD
10-{N-[3-(3-GPro)Benzoyl]-L-seryl}-1,5,10-TAD
10-{N-[4-(3-GPro)Benzoyl]glycyl}-1,5,10-TAD
10-{N-[4-(3-GPro)Benzoyl]-L-seryl}-1,5,10-TAD
10-{N-[2-Chloro-4-(3-GPro)benzoyl]glycyl}-1,5,10-TAD
10-{N-[2-Chloro-4-(3-GPro)benzoyl]-L-seryl}-1,5,10-TAD
10-{N-[3-Chloro-4-(3-GPro)benzoyl]glycyl}-1,5,10-TAD
10-{N-[3-Chloro-4-(3-GPro)benzoyl]-L-seryl}-1,5,10-TAD
10-{N-[3-(4-(3-GPro)Phenyl)propanoyl]glycyl}-1,5,10-TAD
10-{N-[3-(4-(3-GPro)Phenyl)propanoyl]-L-seryl}-1,5,10-TAD
10-{N-[3-(2-Chloro-4-(3-GPro)phenyl)propanoyl]-glycyl}- 1,5,10-TAD
10-{N-[3-(2-Chloro-4-(3-GPro)phenyl)propanoyl]-L-ceryl}-1,5,10-TAD
10-{N-[3-(3-Chloro-4-(3-GPro)phenyl)propanoyl]-glycyl}-1,5,10-TAD
10-{N-[3-(3-Chloro-4-(3-GPro)phenyl)propanoyl]-L-ceryl}-1,5,10-TAD.

The Spergualin-related compounds of formula (I) form salts with acids. Salt-forming acids may be inorganic or organic so long as they are non-toxic. Any non-toxic inorganic acids may be used, but hydrochloric acid, sulfuric acid, nitric acid and phosphoric acid are preferred. While there is also no particular limitation on the organic acids used, the preferred ones are acetic acid, propionic acid, succinic acid, fumaric acid, maleic acid, malic acid, tartaric acid, glutaric acid, citric acid, benzenesulfonic acid, toluenesulfonic acid, methanesulfonic acid, ethanesulfonic acid, propanesulfonic acid, aspartic acid and glutamic acid.

The Spergualin-related compounds of formula (I) of the present invention may be prepared from protected Spergualin-related compounds of formula (II) by removing the protecting groups in a known manner.

The symbols X, m and n in formula (II) representing the starting compound have the same meanings as defined in connection with the compounds of formula (I). The symbol $R'_1$ may have a hydroxymethyl group as a substituent, and if necessary, the hydroxyl group may be protected by an ordinary protecting group. Any known protective groups may be used, and for illustrative examples, see "Protein Chemistry I: Amino acids. Peptides", ed. by Shiro Akabori, Takeo Kaneko and Kozo Narita, Kyoritsu Shuppan, 1969; "Peptide Synthesis", ed. by Nobuo Izumiya, Maruzen, 1975, E. Schröder and K. Lubke; "The Peptides", Academic Press, New York, 1965; E. Wüsch; "Methoden der Organischem Chemie (Houben. Weyl), Syntheses von Peptiden", Georg Thime Verlag Stuttgart, 1974, M. Bodanszky and M. A. Ondetti; "Peptide Synthesis", Interscience Publishers, New York, 1976.

Any known amino protecting groups (see the references listed above) may be used as $R_2$ and as the protecting group on the amino group $R_3$. The $R_2$ and the group protecting on the amino group $R_3$ need not be the same as each other and different groups may be used in proper combinations. However, in order to ensure the ease of handling, the two groups are preferably the same. Illustrative amino- or hydroxy-protecting groups include (1) an optionally substituted $C_1-C_5$ acyl groups, (2) a phenyl mono- or dicarbonyl group such as benzoyl or phthalyl, (3) an optionally substituted $C_1-C_5$ alkoxy carbonyl group, (4) an optionally substituted $C_1-C_5$ alkyl group, (5) an optionally substituted phenylthio or $C_1-C_3$ alkylthio group, and (6) an optionally substituted phenylsulfonyl group. Illustrative substituents on the alkyl or alkoxy group of these groups include a halogen atom, a nitro group, and a substituted or unsubstituted phenyl group. Illustrative substituents on the phenyl group include a halogen atom, a nitro group, a $C_1-C_3$ alkoxy group, a $C_1-C_3$ alkyl group, an optionally substituted phenylazo group. The protecting group of hydroxy is for example, (1) a benzyl group, (2) a benzyloxycarbonyl group, (3) acetyl group, (4) t-butyl group, (5) triphenylmethyl group, (6) 2-pyranyl group or (7) p-methylphenylsulfonyl group, and $R_2$ and the protecting group of amino group of $R_3$ is, for example, (1) formyl group or trifluoroacetyl group, (2) benzoyl group or phthalyl group, (3)(a) t-butoxycarbonyl group, 1-methylethoxycarbonyl group or 1-ethylpropoxycarbonyl group, (b) unsubstituted benzyloxycarbonyl group or benzyloxycarbonyl group substituted by a methoxy group, a halogen atom, a nitro group, a phenylazo group or a phenylazo group substituted by methyl group, (4) a benzyl group or triphenylmethyl group, (5) a o-nitrophenylthio group, (6) a triphenylmethylthio group, or (7) a p-methylphenylsulfonyl group.

The method for removing the protecting groups from the protected Spergualin-related compounds of formula (II) varies with the type of the protecting group used, but any of the known methods (see, for example, the references listed above) may be used.

The protecting groups may be removed at temperatures not higher than the boiling point of the solvent used, and they vary with the type of the protecting groups or the type of the solvent. The temperature is generally in the range of $-50°$ C. to $150°$ C., preferably from $-40°$ C. to $120°$ C. Suitable solvents may be inorganic or organic. Illustrative inorganic solvents include water, liquid ammonia and liquid hydrogen fluoride; illustrative organic solvents include a polar solvent such as $C_1-C_4$ alcohols, acetic acid, dimethylformamide and dioxane, as well as lower alkyl esters of acetic acid. These solvents may be used in admixtures, if required.

Depending upon the type of the protecting groups to be removed, the proper method should be selected from among reduction (e.g. catalytic reduction or reduction with an alkali metal and ammonia), hydrolysis, acid decomposition and hydrazine decomposition. Preferred protecting groups and preferred methods for their removal are listed in Table 1.

In Table 1, the symbol "plus" indicates the removability of a specific protecting group, and a method marked "+" should be used for removing that protecting group. The symbol "minus" indicates that a specific protecting group cannot be removed with the method marked "−". The symbol "±" shows that a specific protecting group is partly removed or decomposed, and the method marked this symbol is unsuitable for removing that particular protecting group.

The protecting groups that can be used in the present invention are not limited to those listed in Table 1, and any of the groups that are shown in the reference cited above on peptide chemistry may be employed.

TABLE 1
Protecting groups on amino functional group and methods for their removal[a]

| Method of removal | | | | | | | | | | | |
|---|---|---|---|---|---|---|---|---|---|---|---|
| Abbrev. | H₂/Pd | Na/NH₃ | HBr/AcOH | HCl | AcOH | CF₃COOH | NH₂NH₂ | NaOH | NH₄OH | HF | CF₃SO₃H |
| Remover | H₂ in the presence of Pd | metallic Na | hydrogen bromide | hydrogen chloride | acetic acid | trifluoro-acetic acid | hydrazine | sodium hydroxide | ammonia | liquid hydrogen fluoride | trifluoro-methane-sulfonic acid |
| Solvent | lower alcohol, dimethylformamide, acetic acid | liquid ammonia | acetic acid | ethyl acetate, lower alcohol, acetic acid, dioxane | acetic acid | trifluoro-acetic acid | lower alcohol | water, lower alcohol | water, lower alcohol | liquid hydrogen fluoride | trifluoro-acetic acid, anisole |
| Temperature[b] Pressure[c] | RT~50° C. atm. ~100 kg/cm² | ≦−30° C. atm. | 0° C.~50° C. atm. | 0° C.~RT atm. | 0° C.~bp atm. | 0° C.~RT atm. | RT~bp atm. | 0° C.~50° C. atm. | 0° C.~50° C. atm. | ≦20° C. atm. | RT atm. |
| Amino protecting group | | | | | | | | | | | |
| C₆H₅CH₂OCO— | + | + | + | ± | − | ± | − | − | − | + | + |
| (CH₃)₃COCO— | − | − | + | + | ± | + | − | − | − | + | + |
| (C₆H₅)₃C— | + | + | ± | + | + | + | − | − | − | − | ± |
| 4-CH₃-C₆H₄-SO₂— | − | + | − | − | − | − | − | − | − | − | − |
| HCO— | − | ± | − | ± | − | − | ± | − | ± | − | − |
| phthaloyl (1,2-C₆H₄(CO)₂) | − | + | − | + | − | − | + | ± | − | − | − |
| CF₃CO— | + | + | + | + | − | − | − | ± | + | − | + |
| 4-CH₃O-C₆H₄-CH₂OCO— | + | + | + | − | − | + | − | − | − | − | − |
| 4-R-C₆H₄-CH₂OCO— | + | + | − | − | − | − | − | − | − | − | − |
| C₆H₅CH₂— | + | + | − | − | − | − | − | − | − | − | − |

TABLE 1-continued

Protecting groups on amino functional group and methods for their removal[a]

| Protecting group | | | | | | | | | | | |
|---|---|---|---|---|---|---|---|---|---|---|---|
| CH$_2$—CH$_2$\\CHOCO—\\CH$_2$—CH$_2$/ | − | | | + | | − | − | | | + | |
| (C$_6$H$_5$)$_2$CHOCO— | + | | | + | + | + | | | + | | |
| ⟨S—C$_6$H$_4$-NO$_2$⟩— | | | | + | + | | | | | + | |
| (C$_6$H$_5$)$_3$C—S— | | | | | + | − | | | + | | |
| (CH$_3$)$_2$CHOCO— | | | | ± | − | − | | ± | | | |
| Hydroxyl protecting group | | | | | | | | | | | |
| CH$_3$CO— | − | − | | − | − | − | | | − | | |
| C$_6$H$_5$CO— (phenolic) | + | + | | + | − | − | | | + | + | |
| (CH$_3$)$_3$C— | | | | − | + | + | + | | + | + | + |
| C$_6$H$_5$CH$_2$— | + | + | | + | − | − | − | | + | + | ± |
| ⟨C$_6$H$_4$-SO$_2$⟩-CH$_3$ (phenolic) | | | + | − | + | | | | − | + | + |
| tetrahydropyranyl | + | + | | + | + | − | | | + | + | + |
| C$_6$H$_5$CH$_2$OCO— (phenolic) | + | + | | + | + | | − | | + | + | + |
| (C$_6$H$_5$)$_3$C— | | | | + | + | | + | | + | | |

[a]R = Cl, Br, NO$_2$, —N=N, CH$_3$, —N=N—⟨C$_6$H$_4$⟩

[b]RT: Room temperature
[c]atm.: atmospheric

The method for isolating the Spergualin-related compounds of formula (I) from the reaction mixture that has been freed of the protecting groups varies with the specific method of removing the protecting groups. If the protecting groups have been removed by catalytic reduction with palladium black, the Spergualin-related compound can be isolated by a method which comprises filtering off the catalyst, concentrating the filtrate under vacuum and purifying the residue by a known method using CM-Cephadex ® (Na+) and Sephadex ® LH-20 [see T. Takeuchi et al., J. Antibiotics, 34, 1619 (1981)]. If the protecting groups have been removed with trifluoroacetic acid, the isolation method consists of concentrating the reaction mixture under vacuum and purifying the residue by a known method as shown above.

By using one of the purifying methods shown above, the Spergualin-related compounds of formula (I) are obtained as hydrochlorides. If other forms of salt are desired, the following procedure may be employed: the hydrochloride is dissolved in water, the resulting aqueous solution is passed through a strong basic ion exchange resin, the fractions containing the end compound are combined, and neutralized by the corresponding acid, an aqueous solution containing the same or its solution in a hydrophilic organic solvent such as methanol, ethanol, acetone, tetrahydrofuran or dioxane, and the neutralized solution is evaporated to dryness under vacuum. Any residual organic solvent is distilled off under vacuum, and the residue is freeze-dried. Alternatively, an aqueous solution of silver hydroxide or silver oxide is added to the hydrochloride salt of the compound of formula (I) for neutralizing the hydrochloric acid, and after filtering off the insoluble silver chloride, a corresponding acid is added to form a salt which is then freeze-dried.

Typical examples of the protected Spergualin-related compound of formula (II) are listed below, wherein diZ and diBOC are the abbreviations for "dibenzyloxycarbonyl" and "di-tert-butyloxycarbonyl", respectively:

10-{N-[4-(3-GP)Butanoyl]glycyl}-1,5-diZ-1,5,10-TAD
10-{N-[4-(3-GP)Butanoyl]glycyl}-1,5-diBOC-1,5,10-TAD
10-{N-[4-(3-GP)Butanoyl]-O-benzyl-L-seryl}-1,5-diZ-1,5,10-TAD
10-{N-[4-(3-GP)Butanoyl]-O-tert-butyl-L-seryl}-1,5-diBOC-1,5,10-TAD
10-{N-[4-(4-GP)Butanoyl]glycyl}-1,5-diZ-1,5,10-TAD
10-{N-[4-(4-GP)Butanoyl]glycyl}-1,5-diBOC-1,5,10-TAD
10-{N-[4-(4-GP)Butanoyl]-O-benzyl-L-ceryl}-1,5-diZ-1,5,10-TAD
10-{N-[4-(4-GP)Butanoyl]-O-tert-butyl-L-ceryl}-1,5-diBOC-1,5,10-TAD
10-{N-[4-(4-GP)Butanoyl]-β-alanyl}-1,5-diZ-1,5,10-TAD
10-{N-[4-(4-GP)Butanoyl]-γ-aminobutanoyl}-1,5-diZ-1,5,10-TAD
10-{N-[4-(2-Chloro-4-GP)butanoyl]glycyl}-1,5-diZ-1,5,10-TAD
10-{N-[4-(2-Chloro-4-GP)butanoyl]-O-benzyl-L-seryl}-1,5-diZ-1,5,10-TAD
10-{N-[4-(2-Chloro-4-GP)butanoyl]-γ-aminobutanoyl}-1,5-diZ-1,5,10-TAD
10-{N-[4-(3-Chloro-4-GP)butanoyl]glycyl}-1,5-diZ-1,5,10-TAD
10-{N-[4-(3-Chloro-4-GP)butanoyl]-O-benzyl-L-seryl}-1,5-diZ-1,5,10-TAD
10-{N-[4-(3-Chloro-4-GP)butanoyl]-β-alanyl}-1,5-diZ-1,5,10-TAD
10-{N-[4-(2-Fluoro-4-GP)butanoyl]glycyl}-1,5,-diZ-1,5,10-TAD
10-{N-[4-(2-Fluoro-4-GP)butanoyl]-O-benzyl-L-seryl}-1,5-diZ-1,5,10-TAD
10-{N-[4-(3-Fluoro-4-GP)butanoyl]glycyl}-1,5-diZ-1,5,10-TAD
10-{N-[4-(3-Fluoro-4-GP)butanoyl]-O-benzyl-L-seryl}-1,5-diZ-1,5,10-TAD
10-{N-[5-(4-GP)Pentanoyl]-O-benzyl-L-seryl}-1,5-diZ-1,5,10-TAD
10-{N-[5-(2-Chloro-4-GP)pentanoyl]glycyl}-1,5-diZ-1,5,10-TAD
10-{N-[5-(3-Chloro-4-GP)pentanoyl]glycyl}-1,5-diZ-1,5,10-TAD
10-{N-[5-(3-Chloro-4-GP)pentanoyl]-O-benzyl-L-seryl}-1,5-diZ-1,5,10-TAD
10-{N-[6-(4-GP)Hexanoyl]glycyl}-1,5-diZ-1,5,10-TAD
10-{N-[6-(4-GP)Hexanoyl]-O-benzyl-L-seryl}-1,5-diZ-1,5,10-TAD
10-{N-[6-(3-Chloro-4-GP)hexanoyl]-O-benzyl-L-seryl}-1,5-diZ-1,5,10-TAD
10-{N-[3-(3-GMP)Propanoyl]-O-benzyl-L-seryl}-1,5-diZ-1,5,10-TAD
10-{N-[3-(4-GMP)Propanoyl]-O-benzyl-L-seryl}-1,5-diZ-1,5,10-TAD
10-{N-[3-(2-Chloro-4-GMP)propanoyl]glycyl}-1,5-diZ-1,5,10-TAD
10-{N-[3-(2-Chloro-4-GMP)propanoyl]-O-benzyl-L-seryl}-1,5-diZ-1,5,10-TAD
10-{N-[3-(3-Chloro-4-GMP)propanoyl]glycyl}-1,5-diZ-1,5,10-TAD
10-{N-[3-(3-Chloro-4-GMP)propanoyl]-O-benzyl-L-seryl}-1,5-diZ-1,5,10-TAD
10-{N-[4-(4-GMP)Butanoyl]glycyl}-1,5-diZ-1,5,10-TAD
10-{N-[4-(4-GMP)Butanoyl]-O-benzyl-L-ceryl}-1,5-diZ-1,5,10-TAD
10-{N-[4-(3-Chloro-4-GMP)butanoyl]-O-benzyl-L-seryl}-1,5-diZ-1,5,10-TAD
10-{N-[5-(2-GMP)Pentanoyl]-O-benzyl-L-seryl}-1,5-diZ-1,5,10-TAD
10-{N-[5-(4-GMP)Pentanoyl]glycyl}-1,5-diZ-1,5,10-TAD
10-{N-[5-(2-Chloro-4-GMP)pentanoyl]glycyl}-1,5-diZ-1,5,10-TAD
10-{N-[5-(2-Chloro-4-GMP)pentanoyl]-O-benzyl-L-seryl}-1,5-diZ-1,5,10-TAD
10-{N-[3-(3-GPro)Benzoyl]glycyl}-1,5-diZ-1,5,10-TAD
10-{N-[3-(3-GPro)Benzoyl]glycyl}-O-benzyl-L-seryl}-1,5-diZ-1,5,10-TAD
10-{N-[4-(3-GPro)Benzoyl]glycyl}-1,5-diZ-1,5,10-TAD
10-{N-[4-(3-GPro)Benzoyl]-O-benzyl-L-seryl}-1,5-diZ-1,5,10-TAD
10-{N-[2-Chloro-4-(3-GPro)benzoyl]glycyl}-1,5-diZ-1,5,10-TAD
10-{N-[2-Chloro-4-(3-GPro)benzoyl]-O-benzyl-L-seryl}-1,5-diZ-1,5,10-TAD
10-{N-[3-(4-(3-GPro)Phenyl)propanoyl]glycyl}-1,5-diZ-1,5,10-TAD
10-{N-[3-(4-(3-GPro)Phenyl)propanoyl]-O-benzyl-L-seryl}-1,5-diZ-1,5,10-TAD
10-{N-[3-(2-Chloro-4-(3-GPro)phenyl)propanoyl]glycyl}-1,5-diZ-1,5,10-TAD 10-{N-[3-(2-Chloro-4-(3-GPro)phenyl)propanoyl]-O-benzyl-L-seryl}-1,5-diZ-1,5,10-TAD
10-{N-[3-(3-Chloro-4-(3-GPro)phenyl)propanoyl]-glycyl}-1,5-diZ-1,5,10-TAD
10-{N-[3-(3-Chloro-4-(3-GPro)phenyl)propanoyl]-O-benzyl-L-seryl}-1,5-diZ-1,5,10-TAD The protected Spergualin-related compounds of formula (II) used as the starting material for preparing the end compound of the present invention are novel and may be synthesized by the following method. First, 1,5-di-protected-1,5-10-TAD of the following formula:

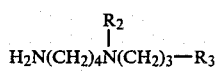  (IV)

(wherein $R_2$ and $R_3$ are the same as defined above) is reacted with a reactive derivative of N-protected, α-, β- or γ-amino acid of the following formula:

$R_5—R_6—COOH$   (V)

(wherein $R_5$ represents an amino protecting group which differs from $R_2$ and the amino protecting group in $R_3$; $R_6$ is α-, β- or γ-aminoalkyl group which may have a hydroxymethyl group as a substituent and wherein the hydroxyl group may be optionally protected), so as to obtain 10-(N-protected aminoacyl)-1,5-di-protected-1,5,10-TAD of the following formula:

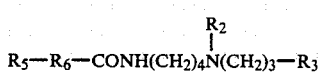  (VI)

(wherein $R_2$, $R_3$, $R_5$ and $R_6$ are the same as defined above), from which the protecting group $R_5$ is removed to obtain 10-aminoacyl-1,5-di-protected-1,5,10-TAD of the following formula:

  (VII)

(wherein $R'_1$, $R_2$ and $R_3$ are the same as defined above), which is further reacted with a reactive derivative of ω-guanidinocarboxylic acid which contains a phenylene group to obtain the compound represented by the following formula:

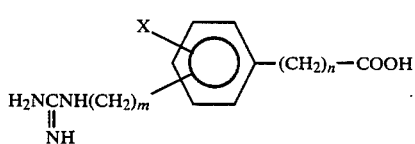  (A)

(wherein m, n and X are the same as defined above), thereby synthesizing the protected Spergualin-related compound of formula (II).

The compound of formula (VII) may be condensed with the compound of formula (A) by any conventional method that is used in the formation of a peptide bond. Illustrative examples include the following: the acid chloride method, the carbodiimide method using dicyclohexylcarbodiimide or 1-ethyl-3-(3-dimethylaminopropyl)-carbodiimide, the azide method using hydrazide, the mixed acid anhydride method using ethyl chlorocarbonate or isobutyl chlorocarbonate, the active ester method using a cyanomethyl ester, vinyl ester, substituted or unsubstituted phenyl ester, thiophenyl ester or N-hydroxysuccinimido ester, the O-acylhydroxylamine derivative method using acetoxime or cyclohexanone oxime, and the N-acyl compound method using carbonyl diimidazole. The condensation solvent may be selected from among any ordinary solvents used in the formation of peptide bond. Illustrative solvents include ethers such as diethyl ether, tetrahydrofuran and dioxane, ketones such as acetone and methyl ethyl ketone, halogenated hydrocarbons such as methylene chloride and chloroform, amides such as dimethylformamide and dimethylacetamide, and nitriles such as acetonitrile. Examples of the ω-guanidinocarboxylic acid of formula (A) include the following: 4-(3 or 4-GP)butyric acid, 4-(2 or 3-chloro-4-GP)butyric acid, 4-(2 or 3-fluoro-4-GP)butyric acid, 5-(3 or 4-GP)valeric acid, 5-(2 or 3-chloro-4-GP)valeric acid, 6-(2 or 3-chloro or fluoro-4-GP)caproic acid, 3-(3 or 4-GMP)propionic acid, 3-(2 or 3-chloro or fluoro-4-GMP)propionic acid, 4-(3 or 4-GMP)butyric acid, 4-(2 or 3-chloro or fluoro-4-GMP)butyric acid, 5-(2,3 or 4-GMP)valeric acid, 5-(2 or 3-chloro or fluoro-4-GMP)valeric acid, 3 or 4-(3-GPro)benzoic acid, 2 or 3-chloro or fluoro-(3-GPro)benzoic acid, 3-[3 or 4-(3-GPro)phenyl]-propionic acid, and 3-[2 or 3-chloro or fluoro-4-(3-GPro)phenyl]-propionic acid. These ω-guanidinocarboxylic acids are synthesized by treating ω-amino acid of the formula:

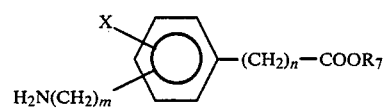  (B)

(wherein $R_7$ represents hydrogen atom or a lower alkyl group and m, n and X are the same as defined above) with a conventional guanidino group forming agent to convert the amino group into a guanidino group. The resulting product is subsequently hydrolyzed if $R_7$ in formula (B) is a lower alkyl group. Some of the ω-amino acids of the formula (B) are also novel compounds, and they may be synthesized from different starting materials by combining known methods of synthesis.

Examples of the starting compound of the formula (VII) are listed below:
10-Glycyl-1,5-diZ-1,5,10-TAD
10-Glycyl-1,5-diBOC-1,5,10-TAD
10-(O-Benzyl-L-ceryl)-1,5-diZ-1,5,10-TAD
10-(O-tert-Butyl-L-ceryl)-1,5-diBOC-1,5,10-TAD
10-β-Alanyl-1,5-diZ-1,5,10-TAD
10-β-Alanyl-1,5-diBOC-1,5,10-TAD
10-γ-Aminobutanoyl-1,5-diZ-1,5,10-TAD
10-γ-Aminobutanoyl-1,5-diBOC-1,5,10-TAD The prefered compounds in the general formula (I) are as follows:

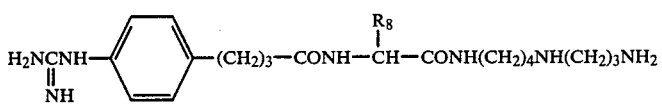

(VIII)

wherein $R_8$ is a hydrogen atom or a hydroxymethyl group and non-toxic salt thereof.

The compounds of the formula (VIII) are produced by removing the protecting groups from a protected Spergualin-related compound represented by the general formula

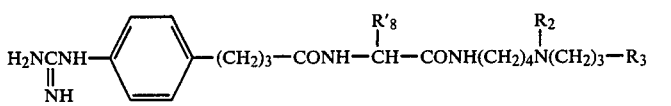

(IX)

wherein $R'_8$ is a hydrogen atom or a protected hydroxymethyl group, $R_2$ is an amino protecting group and $R_3$ is a protected amino group.

The present invention is hereunder described in more detail by reference to working examples. The Rf values for thin-layer chromatography (TLC) listed in the following examples were measured by the following procedure: a silica gel 60 $F_{254}$ plate (thickness: 0.25 mm, product of Merck & Co.) was developed about 8 cm with the solvent systems listed, and the distance from the origin point and the center of the spot of the object compound was divided by the distance between the origin point and the front end of the solvent. Detection was done by UV (2537 Å) variation or by coloration with ninhydrin or Sakaguchi's reagent.

EXAMPLE 1

10-{N-[4-(4-GP)Butanoyl]-L-seryl}-1,5,10-TAD trihydrochloride (Compound No. 1)

A pale yellow oil of 10-{N-[4-(4-GP)butanoyl]-O-benzyl-L-seryl}-1,5-diZ-1,5,10-TAD hydrochloride (4.06 g, 4.89 mmol) was dissolved in a mixture of methanol (50 ml) and acetic acid (30 ml). Palladium black (0.4 g) was added to the solution, which was heated at 55° C. to effect catalytic reduction for 6 hours at atmospheric pressure. After the reaction, the catalyst was filtered off, and the filtrate was concentrated under vacuum to give an oil (2.80 g). This oil was dissolved in 25 ml of the mixed solvent of methanol (60 parts) and 0.3M sodium chloride aqueous solution (40 parts) and the solution was passed through a column packed with 350 ml of CM-Sephadex ® C-25 (Na+) that had been equilibrated with the same solvent.

Elution was conducted by the gradient elution method between 2000 ml of the mixture of methanol (60 parts) and 0.3M sodium chloride aqueous solution (40 parts) and 2000 ml of the mixture of methanol (60 parts) and 1.0M sodium chloride aqueous solution (40 parts). The fractions containing the end compound were combined, and evaporated to dryness under vacuum. Methanol was added to the residue and the insoluble sodium chloride was filtered off. The object compound was purified from the oily product by the following procedure. In order to remove the remaining small amount of sodium chloride, the oily product was dissolved in methanol (5 ml), and the solution was passed through a column packed with 100 ml of Sephadex ® LH-20. The column was eluted with methanol, and the fractions containing the object compound were combined and concentrated under vacuum. In order to further remove the small amount of impurities, the oily product was dissolved in 5 ml of distilled water, and the solution was passed through a column packed with 80 ml of HP-20 ® (Mitsubishi Chemical Industries, Ltd.). The column was eluted with distilled water, and the fractions containing the object compound were combined and concentrated under vacuum. The resulting oily product was dissolved in distilled water (5 ml), and the insoluble matter was filtered off. The filtrate was freeze-dried to obtain 1.17 g of the object compound (yield: 44.0%).

NMR (DMSO-$d_6$)
$\delta = 1.1$–2.5 (b, 12H), 2.5–3.4 (b, 8H), 3.4–3.8 (bd, 3H), 4.0–4.5 (b, 1H), 6.8–7.7 (m, 8H), 7.7–8.8 (b, 5H), 8.8–9.7 (b, 2H), 10.13 (bs, 1H).

IR (KBr)
$\nu(cm^{-1}) = 3290, 2940, 2320, 1635, 1510, 1450$.

TLC (n-propanol:pyridine:water:acetic acid = 6:4:3:2 v/v)
Rf = 0.34
$[\alpha]_D^{19.5} - 13.8°$ (c = 1.17, $H_2O$).

In this Example, 10-(N-[4-(4-GP)butanoyl]-O-tert butyl-L-seryl}-1,5-diZ-1,5,10-TAD hydrochloride instead of 10-{N-[4-(4-GP)butanoyl]-O-benzyl-L-seryl}-1,5-diZ-1,5,10-TAD was used.

10-{N-[4-(4-GP)butanoyl]-O-tert-butyl-L-seryl}-1,5-diZ-1,5,10-TAD hydrochloride was treated by trifluoroacetic acid and then the products was reduced and purified by procedures similar to those used in this Example to obtain the object compound.

In this Example, 10-{N-[4-(4-GP)butanoyl]-O-acetyl-L-seryl}-1,5-diZ-1,5,10-TAD hydrochloride instead of 10-{N-[4-(4-GP)butanoyl]-O-benzyl-L-seryl}-1,5-diZ-1,5,10-TAD hydrochloride was used.

10-{N-[4-(4-GP)butanoyl]-O-acetyl-L-seryl}-1,5-diZ- 1,5,10-TAD hydrochloride was treated by an aqueous solution of sodium hydroxide (1–2 equivalent concentration) and then the product was reduced and purified by procedures similar to those used in this Example to obtain the object compound.

EXAMPLE 2

10-{N-[4-(4-GP)Butanoyl]glycyl}-1,5,10-TAD trihydrochloride (Compound No. 2)

A pale yellow oil of 10-{N-[4-(4-GP)butanoyl]-glycyl}-1,5-diZ-1,5,10-TAD (3.30 g, 4.90 mmol) was dissolved in 40 ml of acetic acid. Palladium black (0.3 g) was added to the solution, which was heated at 50° C. to effect catalytic reduction for 10 hours at atmospheric pressure. After the reaction, the catalyst was filtered off, and the filtrate was concentrated under vacuum to give an oil (2.10 g). This oil was dissolved in distilled water (10 ml) and the solution was passed through a column packed with 220 ml of CM-Sephadex ® C-25

($Na^+$). The column was eluted by the gradient elution method between 1100 ml of distilled water and 1100 ml of 1.0M sodium chloride aqueous solution. The fractions containing the object compound were combined, and concentrated to dryness under vacuum. Methanol was added to the dry solid product, and the insoluble sodium chloride was filtered off.

The product was purified by procedures similar to those used in Example 1, and 0.89 g of the object compound was obtained (yield: 35.3%).

NMR (DMSO-$d_6$)

$\delta$ = 1.1–2.5 (b, 12H), 2.5–3.3 (b, 8H), 3.5–3.9 (bd, 2H), 6.9–7.7 (m, 8H), 7.7–8.3 (b, 3H), 8.3–10.0 (b, 5H).

IR (KBr)

$\nu(cm^{-1})$ = 3290, 2940, 2320, 1640, 1540, 1455.

TLC (n-propanol:pyridine:water:acetic acid = 6:4:3:2 v/v)

Rf = 0.26

EXAMPLE 3

10-{N-[3-(4-GMP)Propanoyl]-L-seryl}-1,5,10-TAD trihydrochloride (Compound No. 3)

A pale yellow oil of 10-{N-[3-(4-GMP)propanoyl]-O-benzyl-L-seryl}-1,5-diZ-1,5,10-TAD (2.60 g, 3.27 mmol) was dissolved in a mixture of methanol (40 ml) and acetic acid (30 ml). Palladium black (0.20 g) was added to the solution, which was heated at 55° C. to effect catalytic reduction for 5 hours at atmospheric pressure. After the reaction, the catalyst was filtered off and the filtrate was concentrated under vacuum to give 1.8 g of an oily product. This oil was dissolved in distilled water (10 ml) and the solution was passed through a column packed with 220 ml of CM-Sephadex ® C-25 ($Na^+$). Elution was conducted by the gradient elution method between 1100 ml of distilled water and 1100 ml of 1.2M sodium chloride aqueous solution. The fraction containing the object compound were combined and concentrated to dryness under vacuum. Methanol was added to the dry solid matter and the insoluble sodium chloride was filtered off.

The product was purified by following the procedure used in Example 1, and 0.84 g of the end compound was obtained (yield: 47.2%)

NMR (DMSO-$d_6$)

$\delta$ = 1.1–2.4 (b, 6H), 2.4–3.4 (b, 12H), 3.4–3.9 (bd, 3H), 4.0–4.6 (bd, 3H), 6.8–7.7 (b, 4H), 7.2 (s, 4H), 7.7–8.7 (b, 6H), 8.7–9.7 (b, 2H)

IR (KBr)

$\nu(cm^{-1})$ = 3310, 2940, 2320, 1640, 1535, 1450.

TLC (n-propanol:pyridine:water:acetic acid = 6:4:3:2 v/v)

Rf = 0.25

$[\alpha]_D^{19.5}$ −24.8° (c = 1.0, $H_2O$)

EXAMPLE 4

10-{N-[4-(3-GPro)Benzoyl]-L-seryl}-1,5,10-TAD trihydrochloride (Compound No. 4)

An oil of 10-{N-[4-(3-GPro)benzoyl]-O-benzyl-L-seryl}-1,5-diZ-1,5,10-TAD (2.00 g, 2.52 mmol) was dissolved in a mixture of methanol (4 ml) and acetic acid (20 ml). Palladium black (0.3 g) was added to the solution, which was heated at 50° C. and subjected to catalytic reduction for 6 hours at atmospheric pressure. After the reaction, the catalyst was filtered off and the filtrate was concentrated under vacuum to give 2.60 g of an oil. This oil was dissolved in 10 ml of distilled water, and the solution was passed through a column packed with 300 ml of CM-Sephadex ® C-25 ($Na^+$).

Elution was conducted by the gradient elution method between 1100 ml of distilled water and 1100 ml of 1.3M sodium chloride aqueous solution. The fractions containing the object compound were combined and concentrated to dryness under vacuum. Methanol was added to the residue and the insoluble sodium chloride was filtered off. The resulting product was purified by procedures similar to those used in Example 1, and 0.642 g of the object compound was obtained (yield: 49.9%).

NMR (DMSO-$d_6$)

$\delta$ = 1.2–2.4 (b, 8H), 2.6–3.4 (b, 12H), 3.4–4.2 (bd, 3H), 4.2–4.7 (b, 1H), 7.1–7.5 (b, 4H), 7.33 (d, 2H, J = 8 Hz), 7.7–8.8 (b, 6H), 7.90 (d, 2H, J = 8 Hz), 8.8–9.7 (b, 2H).

IR (KBr)

$\nu(cm^{-1})$ = 3300, 3150, 2950, 1640, 1535, 1500, 1460, 1290, 1060.

TLC (n-propanol:pyridine:water:acetic acid = 6:4:3:2 v/v)

Rf = 0.31

$[\alpha]_D^{19.5}$ +24.4° (c = 0.97, $H_2O$).

EXAMPLE 5

10-{N-[3-(3-GMP)Propanoyl]-L-seryl}-1,5,10-TAD trihydrochloride (Compound No. 5)

A pale yellow oil of 10-{N-3-(3-GMP)propanoyl]-O-benzyl-L-seryl}-1,5-diZ-1,5,10-TAD (1.61 g, 2.03 mmol) was treated as in Example 3, and the object compound was obtained in an amount of 0.54 g (yield: 48.2%).

NMR (DMSO-$d_6$)

$\delta$ = 1.1–2.3 (b, 6H), 2.3–3.4 (b, 12H), 3.4–3.8 (bd, 3H), 4.0–4.6 (bd, 3H), 6.8–7.8 (m, 8H), 7.8–8.8 (b, 6H), 8.8–9.7 (b, 2H).

IR (KBr)

$\nu(cm^{-1})$ = 3240, 2320, 1630, 1530, 1450.

TLC (n-propanol:pyridine:water:acetic acid = 6:4:3:2 v/v)

Rf = 0.30

$[\alpha]_D^{19.5}$ −22.0° (c = 1.0, $H_2O$)

EXAMPLE 6

10-{N-[5-(4-GP)Pentanoyl]-L-seryl}-1,5,10-TAD trihydrochloride (Compound No. 6)

A pale yellow oil of 10-{N-[5-(4-GP)pentanoyl]-O-benzyl-L-seryl}-1,5-diZ-1,5,10-TAD (2.42 g, 3.00 mmol) was treated as in Example 3, and the object compound was obtained in an amount of 0.69 g (yield: 41.1%).

NMR (DMSO-$d_6$)

$\delta$ = 1.1–2.5 (b, 14H), 2.5–3.3 (b, 8H), 3.4–3.7 (bd, 3H), 4.0–4.4 (b, 1H), 6.8–7.7 (m, 8H), 7.7–8.7 (b, 5H), 8.7–9.7 (b, 2H), 10.05 (bs, 1H).

IR KBr)

$\nu(cm^{-1})$ = 3300, 2940, 2330, 1640, 1510, 1450.

TLC (n-propanol:pyridine:water:acetic acid = 6:4:3:2 v/v)

Rf = 0.31

$[\alpha]_D^{19.5}$ −13.9° (c = 1.07, $H_2O$)

EXAMPLE 7

10-{N-[4-(3-GPro)Benzoyl]glycyl}-1,5,10-TAD trihydrochloride (Compound No. 7)

An oil of 10-{N-[4-(3-GPro)benzoyl]glycyl}-1,5-diZ-1,5,10-TAD (1.34 g, 1.99 mmol) was dissolved in 5 ml of acetic acid. To the solution, 10 ml of a 25% solution of hydrogenbromide in acetic acid was added under cooling. After 30 min reaction at room temperature under agitation, dry ethyl ether was added, and the precipitating oily product was washed by decantation. This procedure was repeated two more times, and the oil layer was dried under vacuum to give 1.64 g of an oily product. This oily product was subsequently treated as in Example 2 to give 0.427 g of the object compound (yield: 39%).

NMR (DMSO-$d_6$)

$\delta$1.1–2.4 (b, 8H), 2.5–3.4 (b, 12H), 3.7–4.0 (bd, 2H), 7.1–7.5 (b, 4H), 7.33 (d, 2H, J=8 Hz), 7.7–8.5 (b, 8H), 7.90 (d, 2H, J=8 Hz), 8.5–8.9 (b, 1H), 8.9–9.6 (b, 2H).

IR (KBr)

$\nu$(cm$^{-1}$)=3270, 2950, 2930, 1640, 1540, 1500, 1460, 1300.

TLC (n-propanol:pyridine:water:acetic acid=6:4:3:2 v/v)

Rf=0.33

EXAMPLE 8

10-{N-[5-(2-GMP)Pentanoyl]-L-ceryl}-1,5,10-TAD trihydrochloride (Compound No. 8)

A pale yellow oil of 10-{N-[5-(2-GMP)pentanoyl]-O-benzyl-L-seryl}-1,5-diZ-1,5,10-TAD (2.78 g, 3.38 mmol) was treated as in Example 3, and the object compound was produced in an amount of 0.81 g (yield: 41.8%)

NMR (DMSO-$d_6$)

$\delta$=1.1–2.5 (b, 14H), 2.5–3.4 (b, 8H), 3.4–3.8 (bd, 3H), 4.0–4.6 (bd, 3H), 6.8–7.7 (m, 8H), 7.7–8.8 (b, 6H), 8.8–9.6 (b, 2H).

IR (KBr)

$\nu$(cm$^{-1}$)=3280, 2930, 2320, 1640, 1540, 1450.

TLC (n-propanol:pyridine:water:acetic acid=6:4:3:2 v/v)

Rf=0.50

$[\alpha]_D^{19.5}$ −13.9° (c=1.02, H2O)

EXAMPLE 9

10-{N-[3-(2-Chloro-4-GMP)propanoyl]-L-seryl}-1,5,10-TAD trihydrochloride (Compound No. 9)

An oil of 10-{N-[3-(2-chloro-4-GMP)propanoyl]-O-benzyl-L-seryl}-1,5-diZ-1,5,10-TAD ½ phosphate (1.60 g,.1.86 mmol) was mixed with 20 ml of a trifluoroacetic acid solution of trifluoromethanesulfonic acid (3.00 g) and thioanisole (2.48 g) under cooling with ice, and a solution was formed. The solution was subjected to reaction for 2 hours under agitation at room temperature.

After the reaction, dry ether (100 ml) was added, and the separating oil was washed by decantation. This procedure was repeated two more times, and the oily layer was concentrated under vacuum. Distilled water (100 ml) was added to the residue, and the insoluble matter was filtered off. The filtrate was directly passed through a column packed with 300 ml of CM-Sephadex® C-25 (Na+). The column was subsequently treated as in Example 3, and the object compound was produced in an amount of 0.528 g (yield: 49.0%).

NMR (DMSO-$d_6$)

$\delta$=1.2–2.3 (b, 6H), 2.5–3.3 (b, 12H), 3.3–3.7 (bd, 3H), 4.1–4.6 (bd, 3H), 7.1–7.7 (m, 7H), 7.7–8.6 (b, 6H), 8.6–9.5 (b, 2H).

IR (KBr)

$\nu$(cm$^{-1}$)=3300, 3150, 3050, 2950, 1645, 1540, 1450, 1050.

TLC (n-propanol:pyridine:water:acetic acid=6:4:3:2 v/v)

Rf=0.35

$[\alpha]_D^{19.0}$ −26.1° (c=1.1, H2O)

EXAMPLE 10

10-{N-[6-(4-GP)hexanoyl]-L-seryl}-1,5,10-TAD trihydrochloride (Compound No. 10)

1.13 Grams (1.31 mmol) of a pale yellow oil of 10-{N-[6-(4-GP)hexanoyl]-O-benzyl-L-seryl}-1,5-diZ-1,5,10-TAD was treated by the same procedure as used in Example 3 to obtain 0.15 g of the object compound (yield: 63.9%).

MP. 159.5 20 –161.5° C.

NMR (DMSO-$d_6$)

$\delta$=1.00–1.90 (b, 12H), 1.90–2.38 (b, 4H), 2.57–3.22 (b, 8H), 3.22–3.85 (b, 3H), 3.85–4.55 (b, 1H), 4.55–5.38 (b, 1H), 6.95–7.40 (m, 4H), 7.40–7.72 (b, 4H), 7.72–8.15 (b, 2H), 8.15–9.32 (b, 4H), 9.32–10.53 (b, 1H).

IR (Kbr)

$\nu$(cm$^{-1}$)=3280, 2930, 2775, 1640, 1555, 1510, 1450, 1295, 1245, 1060.

TLC (n-propanol:pyridine:water:acetic acid=6:4:3:2 v/v)

Rf=0.43

$[\alpha]_D^{20.5}$ −13.7° (c=1.28, H2O)

Reference Example 1

Synthesis of
10-{N-[4-(4-GP)butanoyl]-O-benzyl-L-seryl}-1,5-diZ-1,5,10-TAD hydrochloride (1)
10-(N-tert-Butoxycarbonyl-O-benzyl-L-seryl)-1,5-diZ-1,5,10-TAD In ethyl acetate (50 ml), 4.76 g (11.5 mmol) of 1,5-diZ-1,5,10-TAD was dissolved, and under cooling with ice, triethylamine (1.04 g, 10.3 mmol) was added. Thereafter, 5.87 g (ca. 15 mmol) of N-tert-butoxycarbonyl-O-benzyl-L-serin-N-hydroxysuccinimide ester was added, and the mixture was subjected to reaction overnight at room temperature. Ethyl acetate (50 ml) was added to the reaction mixture, and the resulting ethyl acetate solution was successively washed with 5% aqueous solution of sodium hydrogencarbonate, 0.1N hydrochloric acid and saturated aqueous sodium chloride. The ethyl acetate layer was dried over anhydrous sodium sulfate, and the desiccant was filtered off. By concentrating the filtrate under vacuum, the object compound was obtained in an amount of 8.34 g (yield: quantitative).

TLC (chloroform:methanol=9:1 v/v)

Rf=0.80.

(2) 10-(O-Benzyl-L-seryl)-1,5-diZ-1,5,10-TAD 10-(N-tert-Butoxycarbonyl-O-benzyl-L-seryl)-1,5-diZ-1,5,10-TAD (8.00 g, 11.5 mmol) was dissolved in trifluoroacetic acid (8.0 ml), and the resulting solution was subjected to reaction for 3 hours at room temperature. The reaction mixture was concentrated under vacuum, and the resulting oily product was dissolved in ethyl acetate (200 ml). The solution was washed successively with 5% sodium hydrogen carbonate solution and distilled water. The ethyl acetate layer was dried over anhydrous sodium sulfate, and the desiccant was filtered off. By concentrating the filtrate under vacuum, an oil of the object compound was produced in an amount of 6.82 g (yield: quantitative).

TLC (chloroform:methanol=9:1 v/v)
Rf=0.50

(3) 10-{N-[4-(4-GP)Butanoyl]-O-benzyl-L-seryl}-1,5-diZ-1,5,10-TAD hydrochloride:

A brown crystal of 4-(4-GP)butyric acid hydrochloride (1.26 g, 4.89 mmol) was dissolved in dimethylformamide (20 ml). To the resulting solution, N-hydroxysuccinimide (0.68 g, 5.87 mmol) and N,N'-dicyclohexylcarbodiimide (1.20 g, 5.87 mmol) was added under cooling, and the mixture was subjected to reaction overnight at room temperature. The precipitated N,N'-dicyclohexylurea was filtered off, and the filtrate was directly used in the next reaction. A pale yellow oil of 10-(O-benzyl-L-seryl)-1,5-diZ-1,5,10-TAD (3.54 g, 6.00 mmol) was dissolved in dimethylformamide (30 ml). To the solution, triethylamine (0.61 g, 6.00 mmol) was added under cooling with ice, followed by the addition of a dimethylformamide solution of the previously prepared 4-(4-GP) butyric acid hydrochloride N-hydroxysuccinimide ester. The resulting mixture was subjected to reaction overnight at room temperature. The reaction mixture was concentrated under vacuum, and the oily residue was dissolved in a mixture of ethyl acetate (150 ml) and chloroform (150 ml). The solution was washed successively with 5% aqueous sodium carbonate solution, 0.5N hydrochloric acid and saturated aqueous sodium chloride. The organic layer was dried over anhydrous sodium sulfate, and the desiccant was filtered off. The filtrate was concentrated under vacuum to give a pale yellow oil of the object compound in an amount of 4.10 g (yield: quantitative).

NMR DMSO-d$_6$)
$\delta$=1.1–2.8 (b, 12H), 2.8–3.8 (b, 10H), 4.2–4.8 (bs, 3H), 5.02 (s, 2H), 5.06 (s, 2H), 7.3 (s, 15H), 7.7–10.1 (b, 12H)
TLC (chloroform:methanol:17% ammonia water=6:1.5:0.25 v/v)
Rf=0.16

The 4-(4-GP)butyric acid hydrochloride was synthesized by the following method.

A brown crystal of 4-(4-aminophenyl)butyric acid (1.60 g, 8.93 mmol) was dissolved in tetrahydrofuran (40 ml). To the resulting solution, 1-amidino-3,5-dimethylpyrazole nitrate (2.70 g, 13.4 mmol) and N,N-diisopropylethylamine (2.19 g, 17.0 mmol) were added, and the mixture was subjected to reaction overnight under reflux. The precipitated crystal was filtered, and the crystal was washed successively with acetone, methanol and tetrahydrofuran, and dried. The dried brown crystal was suspended in distilled water (10 ml), and 1N hydrochloric acid was added until the crystal dissolved completely. Thereafter, the solution was concentrated to dryness under vacuum. The residue was washed twice with each of ether and acetone. A brown crystal was obtained in an amount of 1.54 g (yield: 67.0%). m.p. 157°–160° C.

NMR (D$_2$O+DCl, external TMS)
$\delta$=2.1–2.6 (m, 2H), 2.6–3.3 (m, 4H), 7.5–7.9 (m, 4H),
IR (KBr)
$\nu$(cm$^{-1}$)=3370, 3170, 2330, 1730, 1680, 1660, 1620, 1600, 1575, 1510, 1240, 1220.

Reference Example 2
Synthesis of 10-{N-[4-(4-GP)butanoyl]glycyl}-1,5-diZ-1,5,10-TAD (1) 10-(N,N-Phthalylglycyl)-1,5-diZ-1,5,10-TAD In tetrahydrofuran (200 ml), 1,5-diZ-1,5,10-TAD (12.4 g, 30.0 mmol) was dissolved. To the solution, triethylamine (4.90 ml, 35.0 mmol) was added under cooling with ice, followed by the addition of phthalylglycine N-hydroxysuccinimide ester (10.6 g, 35.0 mmol). The resulting mixture was subjected to reaction overnight at room temperature.

The reaction mixture was evaporated to dryness under vacuum, and the residue was dissolved in ethyl acetate (1200 ml). The ethyl acetate solution was washed successively with 5% aqueous solution of sodium hydrogen carbonate 0.5N hydrochloric acid and saturated aqueous sodium chloride. The ethyl acetate layer was dried over anhydrous sodium sulfate and the desiccant was filtered off. The filtrate was concentrated under vacuum and the residue was crystallized by addition of ethyl acetate and ethyl ether. The crystal was recovered by filtration and dried to give 14.6 g of the object compound (yield: 81.0%).

m.p. 102°–104° C.
TLC (chloroform:methanol:acetic acid=95:5:3 v/v)
Rf=0.4

(2) 10-Glycyl-1,5-diZ-1,5,10-TAD

To 10-(N,N-phthalylglycyl)-1,5-diZ-1,5,10-TAD (14.4 g, 24.0 mmol), ethanol (370 ml) and hydrazine hydrate (6.00 g, 120 mmol) were added, and the mixture was refluxed for 2 hours. After the reaction, the insoluble matter was filtered off, and the filtrate was concentrated under vacuum. The resulting oil was dissolved in ethyl acetate (300 ml), and the solution was washed successively with 5% aqueous solution of sodium hydrogen carbonate and distilled water. The ethyl acetate layer was dried over anhydrous sodium sulfate. After filtering off the desiccant, the filtrate was concentrated under vacuum to give an oil of the object compound in an amount of 12.5 g (yield: quantitative).

TLC (chloroform:methanol:acetic acid=95:5:3 v/v)
Rf=0.10

(3) 10-{N-[4-(4-GP)Butanoyl]glycyl}-1,5-diZ-1,5,10-TAD

A brown crystal of 4-(4-GP)butyric acid hydrochloride (1.56 g, 6.05 mmol) was dissolved in dimethylformamide (20 ml). To the resulting solution, N-hydroxysuccinimide (0.84 g, 7.26 mmol) and N,N'-dicyclohexylcarbodiimide (1.50 g, 7.26 mmol) were added under cooling, and the mixture was subjected to reaction overnight at room temperature. The precipitating N,N'-dicyclohexylurea was filtered off, and the filtrate was directly used in the next reaction.

A pale yellow oil of 10-glycyl-1,5-diZ-1,5,10-TAD (2.59 g, 5.5 mmol) was dissolved in dimethylformamide (30 ml). To the resulting solution, triethylamine (0.61 g, 6.05 mmol) was added under cooling with ice, followed by the addition of a dimethylformamide solution of the previously prepared 4-(4-GP)butyric acid hydrochloride N-hydroxysuccinimide ester, and the mixture was subjected to reaction overnight at room temperature. The reaction mixture was concentrated under vacuum, and the oily residue was dissolved in a mixture of ethyl acetate (300 ml) and ethanol (60 ml). The solution was washed successively with 5% phosphoric acid, 5% aqueous solution of sodium carbonate and saturated aqueous sodium chloride. An oil that precipitated during the washing was dissolved by addition of a small amount of ethanol. The organic layer was dried over anhydrous sodium sulfate, and the desiccant was filtered off. Thereafter, the filtrate was concentrated under vacuum and a pale yellow oil of the object compound was obtained in an amount of 3.30 g (yield: 89.1%).

NMR (CDCl$_3$)

$\delta = 1.1$–2.8 (b, 12H), 2.8–4.1 (b, 10H), 5.04 (s, 4H), 4.8–8.1 (b, 11H), 7.3 (s, 10H).

TLC (chloroform:methanol:17% ammonia water = 6:3.5:1 v/v)

Rf = 0.59

Reference Example 3

Synthesis of 10-{N-[3-(4-GMP)propanoyl]-O-benzyl-L-ceryl}-1,5-diZ-1,5,10-TAD A pale yellow crystal of 3-(4-GMP)propionic acid (1.00 g, 4.52 mmol) was added by portions in thionyl chloride (3 ml) under cooling with ice. Thereafter, the mixture was subjected to reaction for 15 minutes under cooling with ice, and the reaction mixture was concentrated to dryness under vacuum.

In dimethylformamide (10 ml), 10-(O-benzyl-L-seryl)-1,5-diZ-1,5,10-TAD (2.00 g, 3.38 mmol) was dissolved. To the resulting solution, triethylamine (0.92 g, 9.04 mmol) was added, followed by the addition of a dimethylformamide (4 ml) solution of the previously synthesized 3-(4-GMP)-propionic acid chloride hydrochloride. The mixture was subjected to reaction for 30 minutes under cooling with ice. The reaction mixture was concentrated under vacuum, and the oily residue was dissolved in a mixture of ethyl acetate (300 ml) and ethanol (50 ml). The solution was washed successively with 5% phosphoric acid, 5% aqueous solution of sodium carbonate and saturated aqueous sodium chloride. An oily product that precipitated during the washing was dissolved by the addition of a small amount of ethanol. The organic layer was dried over anhydrous sodium sulfate and the desiccant was filtered off. Thereafter, the filtrate was concentrated under vacuum to give 2.67 g of the end compound as a pale yellow oil (yield: quantitative).

NMR (CDCl$_3$)

$\delta = 1.0$–2.0 (b, 6H), 2.0–3.9 (b, 14H), 4.0–4.8 (bd, 5H), 5.0 (s, 2H), 5.05 (s, 2H), 5.1–8.3 (b, 11H), 7.2 (s, 15H).

TLC (chloroform:methanol: 17% ammonia water = 6:1.5:0.25 v/v)

Rf = 0.27

The 3-(4-GMP)propionic acid was synthesized by the following procedure.

(1) Methyl 3-(4-aminomethylphenyl)propionate

Methyl 3-(4-cyanophenyl)propenoate (4.30 g, 22.97 mmol) was dissolved in ammonia saturated methanol (350 ml). After adding 3 g of Raney nickel, the mixture was hydrogenated at room temperature for 2 hours at 60 atm. After the reaction, the catalyst was filtered off, and the filtrate was concentrated under vacuum to give an oil in an amount of 4.02 g (yield: 90.54%).

NMR (CDCl$_3$)

$\delta = 2.4$–3.2 (m, 6H), 3.63 (s, 3H), 3.8–4.7 (b, 2H), 7.16 (s, 4H).

TLC (chloroform:methanol = 10:1 v/v)

Rf = 0.16

(2) 3-(4-GMP)Propionic acid

An oil of methyl 3-(4-aminomethylphenyl)propionate (3.70 g, 19.14 mmol) was dissolved in tetrahydrofuran (150 ml). To the solution, 1-amidino-3,5-dimethylpyrazole nitrate (5.80 g, 28.71 mmol) and N,N-diisopropylethylamine (4.70 g, 36.37 mmol) were added, and the mixture was subjected to reaction overnight under reflux. The reaction mixture was concentrated under vacuum to give an oily product. To this oil, 5% hydrochloric acid (70 ml) was added, and the mixture was subjected to reaction under reflux for 3 hours. The reaction mixture was filtered and the filtrate was cooled with ice. Thereafter, 10% aqueous solution of sodium hydroxide was added to the filtrate to adjust its pH to 6.4. The mixture was agitated gently for 30 minutes under cooling with ice. The precipitating crystal was recovered by filtration and washed first with distilled water, then with tetrahydrolfuran. Upon drying the residue, a pale yellow crystal of the object compound was obtained in an amount of 2.85 g (yield: 67.4%).

m.p. $\geq 300°$ C.

NMR (D$_2$O + DCl, external TMS)

$\delta = 3.0$ - 3.6 (m, 4H), 4.84 (s, 2H), 7.7 (s, 4H).

IR (KBr)

$\nu(cm^{-1}) = 3350, 3060, 2330, 1675, 1610, 1550, 1460, 1405, 1150$

TLC (chloroform:methanol:17% ammonia water = 4:4:2 v/v)

Rf = 0.60

Reference Example 4

Synthesis of 10-{N-[4-(3-GPro)benzoyl]-O-benzyl-L-seryl}-1,5-diZ-1,5,10-TAD 4-(3-GPro)Benzoic acid (0.85 g, 3.84 mmol) was dissolved in thionyl chloride (8.0 ml). After adding a catalytic amount of dry pyridine, the mixture was subjected to reaction under agitation for 6 hours at room temperature. The reaction mixture was concentrated under vacuum. The resulting 4-(3-GPro)benzoic acid chloride hydrochloride was dissolved in dried dimethylformamide (6 ml). The resulting solution was added dropwise to a dry tetrahydrofuran solution (15 ml) of 10-(O-benzyl-L-seryl)-1,5-diZ-1,5,10-TAD (1.90 g, 3.18 mmol) and triethylamine (1.16 g, 11.5 mmol) under cooling with ice. After agitating the mixture for one hour under cooling with ice, several drops of distilled water were added, and the mixture was concentrated under vacuum. The oily residue was dissolved in ethyl acetate (300 ml), and the resulting solution was washed successively with 10% aqueous solution of sodium carbonate, 5% aqueous solution of phosphoric acid, 10% aqueous solution of sodium carbonate, and saturated aqueous sodium chloride. An oil that precipitated during the washing was dissolved by addition of a small amount of ethanol. Subsequently, the organic layer was dried over anhydrous sodium sulfate, and concentrated to dryness under vacuum to give 2.20 g of the object compound as an oil (yield: 87.1%).

NMR (CDCl$_3$)

$\delta = 1.3$–2.1 (b, 8H), 2.5–4.1 (b, 12H), 4.5 (s, 2H), 5.02 (s, 2H), 5.05 (s, 2H), 6.9–8.9 (b, 11H), 7.3 (s, 15H).

TLC (chloroform:methanol:17% ammonia water = 6:1.5:0.25 v/v)

Rf=0.32

The 4-(3-GPro)benzoic acid was synthesized by the following procedure.

Methyl 4-(3-aminopropyl)benzoate (4.00 g, 20.7 mmol) was dissolved in tetrahydrofuran (150 ml). To the resulting solution, 6.25 g (31.0 mmol) of 1-amidino-3,5-dimethylpyrazole nitrate and 5.08 g (39.3 mmol) of N,N-diisopropylethylamine were added, and the mixture was heated under reflux overnight.

The reaction mixture was concentrated under vacuum to give an oily product.

Subsequently, 100 ml of 6N HCl was added to this oil, and the mixture was heated under reflux for 4 hours. The reaction mixture was washed twice with 50 ml of ethyl acetate, and the pH of the aqueous layer was adjusted to 6.0 with 20% aqueous solution of sodium hydroxide. After cooling, the precipitating crystal was recovered by filtration to give the object compound in an amount of 2.53 g (yield: 55.1%).

m.p. 285–289° C.

NMR (DMSO-$d_6$+DCl, external TMS)

$\delta$=2.0–2.7 (m, 2H), 3.1–3.5 (m, 2H), 3.5–4.0 (m, 2H), 7.9 (d, 2H, J=8 Hz), 8.4 (d, 2H, J=8 Hz)

Reference Example 5

Synthesis of 10-{N-[3-(3-GMP)propanoyl]-O-benzyl-L-seryl}-1,5-diZ-1,5,10-TAD

A pale yellow crystal of 3-(3-GMP)propionic acid (0.55 g, 2.49 mmol) and a pale yellow oil of 10-(O-benzyl-L-seryl)-1,5-diZ-1,5,10-TAD (1.20 g, 2.03 mmol) were treated as in Reference Example 3 to give 1.63 g of the end compound as a pale yellow oil (yield: quantitative).

NMR (CDCl$_3$)

$\delta$=1.1–2.1 (b, 6H), 2.1–3.9 (b, 14H), 3.9–4.7 (bd, 5H), 5.0 (s, 2H), 5.05 (s, 2H), 6.3–8.5 (b, 11H), 7.2 (s, 15H)

TLC (chloroform:methanol:17% ammonia water=6:1.5:0.25 v/v)

Rf=0.42

The 3-(3-GMP)propionic acid was synthesized by the following procedure.

(1) Methyl 3-(3-aminomethylphenyl)propionate

A white crystal of methyl 3-(3-cyanophenyl)propionate (4.3 g, 22.97 mmol) was treated as in Reference Example 3-(1), and 4.40 g of the object compound was produced as an oil (yield: quantitative).

NMR (CDCl$_3$)

$\delta$=2.3–3.2 (m, 6H), 3.67 (s, 3H), 4.2–6.5 (b, 2H), 6.7–7.5 (m, 4H).

TLC (chloroform:methanol=10:1 v/v)

Rf=0.24

(2) 3-(3-GMP)Propionic acid

An oil of methyl 3-(3-aminomethylphenyl)propionate (4.40 g, 22.77 mmol) was treated as in Reference Example 3-(2), and 2.1 g of the object compound was produced as a pale yellow crystal (yield: 41.7%). m.p. 273°–276° C.

NMR (D$_2$O+DCl, external TMS)

$\delta$=2.8–3.5 (m, 4H), 4.8 (s, 2H), 7.3–7.9 (m, 4H)

IR (KBr)

$\nu$(cm$^{-1}$)=3340, 3100, 2330, 1645, 1535, 1400, 1330

TLC (chloroform:methanol:17% ammonia water=4:4:2 v/v)

Rf=0.5

Reference Example 6

Synthesis of 10-{N-[5-(4-GP)pentanoyl]-O-benzyl-L-seryl}-1,5-diZ-1,5,10-TAD

A pale yellow crystal of 5-(4-GP)pentanoic acid (0.80 g, 3.40 mmol) and a pale yellow oil of 10-(O-benzyl-L-seryl)-1,5-diZ-1,5,10-TAD (1.80 g, 3.05 mmol) were treated as in Reference Example 3, and 2.42 g of the object compound was produced as a pale yellow oil (yield: quantitative).

NMR (CDCl$_3$)

$\delta$=0.9–2.8 (b, 14H), 2.8–3.9 (b, 10H), 4.47 (bs, 3H), 5.03 (s, 2H), 5.06 (s, 2H), 5.0–7.9 (b, 11H), 7.3 (s, 15H)

TLC (chloroform:methanol:17% ammonia water=6:1.5:0.25 v/v)

Rf=0.38

The 5-(4-GP)pentanoic acid was synthesized by the following procedure.

An oil of methyl 5-(4-aminophenyl)pentanoate (7.42 g, 35.80 mmol) was treated as in Reference Example 3, and a pale yellow crystal of the object compound was obtained in an amount of 3.72 g (yield: 44.1%). m.p. 254°–256° C.

NMR (D$_2$O+DCl, external TMS)

$\delta$=1.7–2.4 (m, 4H), 2.5–3.4 (m, 4H), 7.5–8.0 (m, 4H).

IR (KBr)

$\nu$(cm$^{-1}$)=3330, 2940, 2330, 1680, 1630, 1570, 1515, 1400, 1305, 1265.

TLC (chloroform:methanol:17% ammonia water=4:4:2 v/v)

Rf=0.50

Reference Example 7

10-{N-[4-(3-GP)Benzoyl]glycyl}-1,5-diZ-1,5,10-TAD 4-(3-GPro)benzoic acid (0.66 g, 2.98 mmol) was dissolved in thionyl chloride (6.0 ml). After adding a catalytic amount of dry pyridine, the mixture was subjected to reaction for 4 hours at room temperature under agitation. The reaction mixture was concentrated under vacuum.

The resulting acid chloride hydrochloride was dissolved in dry dimethylformamide (4 ml), and the solution was added dropwise to a dry tetrahydrofuran solution (10 ml) of 10-glycyl-1,5-diZ-1,5,10-TAD (1.27 g, 2.70 mmol) and triethylamine (0.46 g, 4.5 mmol) under cooling with ice.

The mixture was subsequently treated as in Reference Example 4 to give an oil of the object compound in an amount of 1.46 g (yield: 80.3%).

NMR (DMSO-$d_6$)

$\delta$=1.1–2.1 (b, 8H), 2.1–3.5 (b, 12H), 3.7–4.0 (b, 2H), 5.01 (s, 2H), 5.05 (s, 2H), 6.8–8.9 (b, 11H), 7.30 (s, 10H)

TLC (chloroform:methanol:17% ammonia water=6:1.5:0.25 v/v)

Rf=0.34

Reference Example 8

Synthesis of 10-{N-[5-(2-GMP)pentanoyl]-O-benzyl-L-seryl}-1,5-diZ-1,5,10-TAD

A pale yellow crystal of 5-(2-GMP)pentanoic acid (1.20 g, 4.81 mmol) and a pale yellow oil of 10-(O-benzyl-L-seryl)-1,5-diZ-1,5,10-TAD (2.00 g, 3.38 mmol) were treated as in Reference Example 3 to give a pale yellow oil of the object compound in an amount of 2.90 g (yield: quantitative).

NMR (CDCl$_3$)

δ=1.1–2.8 (b, 14H), 2.8–4.0 (b, 10H), 4.2–4.7 (b, 5H), 5.0 (s 2H), 5.04 (s, 2H), 5.0–8.8 (b, 11H), 7.2 (s, 15H)

TLC (chloroform:methanol:17% ammonia water =6:1.5:0.25 v/v)

Rf=0.30

The 5-(2-GMP)pentanoic acid was synthesized by the following procedure.

(1) Methyl 5-(2-cyanophenyl)pentanoate

Methyl 5-(2-cyanophenyl)-2,4-pentadienoate (15.2 g, 71.4 mmol) was dissolved in methanol (600 ml). After adding palladium black (0.6 g), the solution was subjected to catalytic reduction for 6 hours at room temperature and atmospheric pressure. After the reaction, the catalyst was filtered off and the filtrate was concentrated under vacuum to give an oily product in an amount of 16.47 g (yield: quantitative).

NMR (CDCl$_3$)

δ=1.4–2.1 (m, 4H), 2.1–2.6 (m, 2H), 2.6–3.2 (m, 2H), 3.7 (s, 3H), 7.0–7.7 (m, 4H)

(2) Methyl 5-(2-aminomethylphenyl)pentanoate

An oil of methyl 5-(2-cyanophenyl)pentanoate (15.5 g, 71.4 mmol) was treated as in Reference Example 3-(1), and 14.7 g of the object compound was produced as a pale yellow oil (yield: 92.9%).

NMR (CDCl$_3$)

δ=1.35 (s, 2H), 1.3–2.0 (m, 4H), 2.1–2.9 (m, 4H), 3.63 (s, 3H), 3.85 (s, 2H), 7.0–7.5 (m, 4H)

TLC (chloroform:methanol=10:1 v/v)

Rf=0.26

(3) 5-(2-GMP)Pentanoic acid

Methyl 5-(2-aminomethylphenyl)pentanoate (8.00 g, 36.1 mmol) was treated as in Reference Example 3-(2) to give 6.41 g of a pale yellow crystal (yield: 71.2%).

m.p. 275°–277° C.

NMR (D$_2$O+DCl, external TMS)

δ=1.7–2.4 (m, 4H), 2.6–3.3 (m, 4H), 4.8 (s, 2H), 7.5–7.9 (m, 4H).

IR (KBr)

ν(cm$^{-1}$)=3350, 3020, 2950, 2320, 1675, 1620, 1540, 1445, 1395, 1145.

TLC (chloroform:methanol:17% ammonia water =6:3:0.5 v/v)

Rf=0.24

Reference Example 9

Synthesis of 10-{N-[3-(2-chloro-4-GMP)propanoyl]-O-benzyl-L-seryl}-1,5-diZ-1,5,10-TAD 1/3 phosphate 3-(2-Chloro-4-GMP)propionic acid (0.767 g, 3.00 mmol) was dissolved in thionyl chloride (8.0 ml) under cooling. After 30 min reaction under agitation, the solution was concentrated under vacuum. The resulting 3-(2-chloro-4-GMP)propionic acid chloride hydrochloride was dissolved in dry dimethylformamide (10 ml), and the solution was added dropwise to a dry dimethylformamide solution (15 ml) of 10-(O-benzyl-L-seryl)-1,5-diZ-1,5,10-TAD (1.61 g, 2.73 mmol) and triethylamine (0.91 g) under cooling with ice. After 1 hr reaction with stirring under cooling with ice, several drops of distilled water were added to the reaction mixture, which was then concentrated under vacuum. An oily residue was dissolved in a mixture of 300 ml of ethyl acetate and a small amount of ethanol. The solution was washed successively with 5% aqueous solution of sodium carbonate, 5% aqueous solution of phosphoric acid and aqueous sodium chloride. An oil that precipitated during the washing was dissolved by addition of a small amount of ethanol. Subsequently, the organic layer was dried over anhydrous sodium sulfate and concentrated under vacuum to give 1.97 g of the object compound as an oil (yield: 83.8%).

NMR (DMSO-d$_6$)

δ=1.0–2.0 (b, 6H), 2.2–3.5 (b, 12H), 3.5–3.8 (bd, 2H), 4.3–4.8 (bm, 5H), 5.02 (s, 2H), 5.05 (s, 2H), 6.8–8.8 (b, 11H), 7.10 (s, 5H), 7.30 (s, 10H).

TLC (chloroform:methanol:17% ammonia water =6:1.5:0.25 v/v)

Rf=0.21

The 3-(2-chloro-4-GMP)propionic acid was synthesized by the following procedure.

(1) Methyl 3-(2-chloro-4-acetylaminomethylphenyl)-propionate

Methyl 3-(4-acetylaminomethylphenyl)propionate (5.00 g, 21.25 mmol) was added to a sulfuryl chloride (85 ml) solution of anhydrous aluminum chloride (14.2 g, 106 mmol) at −25° C. Thereafter, the temperature of the mixture was gradually elevated to 5° C., at which temperature the mixture was subjected to reaction under agitation for 24 hours.

Subsequently, the reaction mixture was poured onto a large quantity of ice, and the resulting insoluble matter was extracted with chloroform (ca. 1,000 ml). The chloroform layer was washed successively with distilled water, 5% aqueous solution of sodium carbonate, 5% aqueous solution of phosphoric acid and distilled water, and dried over anhydrous magnesium sulfate. Upon concentrating the dried product under vacuum, a brown oil was obtained in an amount of 6.0 g. This oil was subjected to column chromatography on silica gel (Wako Gel C-200, 300 g) and eluted with a toluene-ethyl acetate mixture (1:1 v/v). The fractions containing the object compound were combined and concentrated to dryness to give 1.93 g of the object compound (yield: 33.7%).

m.p. 91°–93° C.

NMR (CDCl$_3$, 400M Hz)

δ=2.03 (s, 3H), 2.63 (t, 2H, J=7.7 Hz), 3.04 (t, 2H, J=7.7 Hz), 3.67 (s, 3H), 4.37 (d, 2H, J=5.9 Hz), 5.85

(bs,, 1H), 7.10 (d, 1H, J=7.8 Hz), 7.20 (d, 1H, J=7.8 Hz), 7.26 (s, 1H).

(2) 3-(2-Chloro-4-aminomethylphenyl)propionic acid hydrochloride

A mixture of 2N hydrochloric acid (20 ml) and dioxane (10 ml) was added to methyl 3-(2-chloro-4-acetylaminomethylphenyl)propionate (1.10 g, 4.08 mmol), and the mixture was heated under reflux for 8 hours. The reaction mixture was then concentrated to dryness under vacuum, whereupon 1.05 g of the object compound was produced as a solid material (yield: quantitative).

m.p. 191°–194° C.
NMR (D$_2$O, external TMS)
δ=2.9–3.7 (m, 4H), 4.60 (s, 2H), 7.6–8.1 (m, 3H).
TLC (chloroform:methanol:17% ammonia water =6:3:0.5 v/v)
Rf=0.20

(3) 3-(2-Chloro-4-GMP)propionic acid 3-(2-Chloro-4-aminomethylphenyl)propionic acid hydrochloride (1.00 g, 4.00 mmol) was dissolved in methanol (40 ml). To the solution, 1-amidino-3,5-dimethylpyrazole nitrate (1.03 g, 5.12 mmol) and N,N-diisopropylethylamine (1.10 g, 8.51 mmol) were added, and the mixture was heated overnight at 80° C. under agitation. The reaction mixture was then concentrated under vacuum, and the residue was dissolved in 100 ml of distilled water. The solution was washed twice with 50 ml of chloroform, and the aqueous layer was adjusted to pH 6.1 with 1N hydrochloric acid. Thereafter, the aqueous layer was concentrated under vacuum.

The residue was washed with acetone, and distilled water. The obtained crystal was dried under vacuum to give 0.75 g of the object compound as a crystal (yield: 73.3%).

m.p. 260°–264° C.
NMR (D$_2$O+DCl, external TMS)
δ=2.8–3.7 (m, 4H), 4.82 (s, 2H), 7.5–7.9 (m, 3H).
TLC (chloroform:methanol:17% ammonia water =6:3:0.5 v/v)
Rf=0.06

Reference Example 10

Synthesis of 10-{N-[6-(4-GP)hexanoyl]-O-benzyl-L-seryl}-1,5-diZ-1,5,10-TAD

A pale yellow crystal of 6-(4-GP)hexanoic acid (0.65 g, 2.61 mmol) and 10-(O-benzyl-L-seryl)-1,5-diZ-1,5,10-TAD (1.29 g, 2.19 mmol) were treated by the procedures similar to those in Reference Example 3 to obtain 1.92 g of the oily object compound (yield: quantitative).

NMR (CDCl$_3$)
δ=0.80–1.95 (b, 14H), 1.95–2.30 (b, 2H), 2.30–2.85 (b, 2H), 2.85–3.45 (b, 8H), 3.45–4.00 (bm, 2H), 4.30–4.80 (b, 1H), 4.67 (s, 2H), 5.05 (s, 4H), 5.60–7.50 (b, 8H), 7.05 (bs, 4H), 7.25 (s, 5H), 7.28 (s, 10H).

IR (Neat)
δ(cm$^{-1}$)=3320, 2940, 1670, 1650, 1540, 1515, 1475, 1450, 1425, 1255, 1210, 740, 700
TLC (chloroform:methanol:17% ammonia water =6:1.5:0.25 v/v)
Rf=0.25

6-(4-GP)Hexanoic acid was produced from methylester of 6-(4-aminophenyl)hexanoic acid by the same process as that for producing 5-(4-GP)pentanoic acid in Reference Example 6.

The data for the stability of the compounds of the present invention in an aqueous solution, for the toxitity in rats and for their life extending efficacy against mouse leukemia L1210 are shown below.

1. Stability of the Compounds of the Present Invention in Aqueous Solution (1) Method of Experiment Each of the compounds of the present invention was dissolved in water to give a concentration of 0.5 (w/w) %. The aqueous solution was held at 40°±1° C. and samples were taken at given intervals. They were subjected to high pressure liquid chromatography and the percent residue was calculated for each sample by measuring the peak area ratio.

(2) Results of Experiment

The percent residue for the compounds of the present invention after the lapse of a given period is shown in Table 2, with the value for the start of the experiment being taken as 100%.

TABLE 2

| Compound | Percent residue for the compounds of the present invention in aqueous solution | | | | | | |
|---|---|---|---|---|---|---|---|
| | Time | | | | | | |
| (Ex. No.) | 0 | 12 | 24 | 48 | 72 | 120 | 168 |
| 1 | 100 | 99.8 | 99.6 | 99.8 | 99.5 | 99.6 | 99.5 |
| 2 | 100 | 99.7 | 99.9 | 99.8 | 99.9 | 100 | 99.8 |
| 3 | 100 | 99.6 | 99.5 | 99.8 | 99.6 | 99.6 | 99.8 |
| 4 | 100 | 99.6 | 99.9 | 99.6 | 99.7 | 99.9 | 99.5 |
| 5 | 100 | 99.9 | 99.6 | 99.6 | 99.9 | 99.6 | 99.8 |
| 6 | 100 | 99.5 | 99.8 | 99.7 | 99.7 | 99.5 | 100 |
| 7 | 100 | 99.6 | 99.6 | 100 | 100 | 99.9 | 99.7 |
| 8 | 100 | 99.7 | 99.9 | 99.5 | 99.8 | 99.7 | 99.8 |
| 9 | 100 | 99.8 | 99.8 | 99.7 | 100 | 99.5 | 99.6 |
| Spergualin | 100 | 94.6 | 90.8 | 84.6 | 78.5 | 69.9 | 65.1 |

2. Ability of the Compounds of the Present Invention to Inhibit In Vitro Growth of Mouse Leukemia L1210 Cells (1) Method of Experiment Leukemia L1210 cells ($1 \times 10^5/0.2$ ml) were transplanted in the intraperitoneal cavity of DBA/2 strain female mice. Four days later, a sample of the abdominal ascites was taken and centrifuged to obtain L1210 cells. These cells were suspended in an RPMI 1640 medium supplemented with fetal bovine serum and 2-mercaptoethanol to have a final concentration of $5 \times 10^4$ cells/0.9 ml.

Each of the compounds of the present invention was dissolved in the medium shown above.

A portion (0.9 ml) of the L1210 cell suspension was mixed with 0.1 ml of the test solution ranging from 0.62 to 1000 μg/ml, and the mixture was incubated in a 5% $CO_2$ atmosphere for 48 hours at 37° C. The cell count was determined both before and after the incubation, and the concentration to inhibit the growth of L1210 cells by 50% of the control (IC$_{50}$) was determined.

(2) Results of Measurement

The ability of typical examples of the compounds of the present invention to inhibit the growth of mouse leukemia L1210 cells is shown in Table 3 in terms of IC$_{50}$.

TABLE 3

Inhibition of in vitro growth of mouse leukemia L 1210 cells by the compounds of the present invention

| Compound (Ex. No.) | IC$_{50}$ (μg/ml) |
|---|---|
| 4 | 1.1 |
| 7 | 0.92 |
| 8 | 0.97 |

3. Toxicity in Rats

(1) Method of Experiment

The compound No. 1 was dissolved in physiological saline (the concentration of the compound No. 1: 6.25 mg/ml). The obtained solution was administered intraperitoneally to rats once a day for 10 consecutive days in a volume of 0.2 ml/100 g (body weight).

Decrease rate of body weight of rats was determined as follows:

Decrease rate of body weight (%) = $\frac{\text{average of body weight of rats after administration}}{\text{average of body weight of rats before administration}} \times 100$

The Results

The results are shown in the attached drawing.

The decrease rate of body weight of rats is very small. Therefore, the toxicity of compound No. 1 is a little.

4. Life Extending Effect of the Compounds of the Present Invention Against Mouse Leukemia L1210 and Their Toxicity

(1) Method of Experiment

Leukemia cells L1210 (1×10$^5$ cells/0.2 ml) were inoculated in the intraperitoneal cavity of CDF$_1$-SLC female mice (6 mice per group). Two compounds of the present invention were each diluted with physiological saline in various concentrations, and starting on the day following the transplantation, each dilution was administered to the mice for 9 consecutive days in a volume of 0.1 ml 10 g (body weight).

30 Days after the inoculation, the mean survival time (day) for each treated group was calculated, and divided by the mean survival time of the control group, and multiplied by 100 to obtain the percent life prolongation (T/C). T/C values greater than 125 are considered to be effective.

(2) Results of Experiment

T/C of typical examples of the compounds of the present invention against mouse leukemia L1210 is shown in Table 4.

TABLE 4

Life extending effect of compounds of the present invention against mouse leukemia L 1210

| Compound (Ex. No.) | Dose (mg/kg/day) | T/C (%) |
|---|---|---|
| Control | 0.00 | 100 |
| 1 | 50.00 | — |
|  | 25.00 | 178 |
|  | 12.50 | 420 |
|  | 6.25 | 435 |
|  | 3.13 | 435 |
|  | 1.56 | 435 |
|  | 0.78 | 406 |
|  | 0.39 | 149 |
| 2 | 50.00 | 15 |
|  | 25.00 | 435 |
|  | 12.50 | 435 |
|  | 6.25 | 435 |
|  | 3.13 | 435 |
|  | 1.56 | 435 |
|  | 0.78 | 145 |
|  | 0.39 | 109 |

What is claimed is:

1. A Spergualin-related compound having a phenylene group, which is represented by the formula

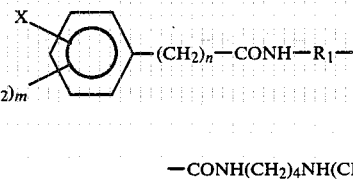

—CONH(CH$_2$)$_4$NH(CH$_2$)$_3$NH$_2$ (wherein R$_1$ is a lower alkylene group which may be substituted by a hydroxymethyl group; X is a hydrogen atom or a halogen atom; m and n are each 0 or an integer of 1 to 5) and a salt thereof.

2. A Spergualin-related compound according to claim 1, wherein R$_1$ is —CH$_2$— or

3. A Spergualin-related compound according to claim 1, wherein m is 0 and n is an integer of 2 to 5.

4. 10-{N-[4-(4-guanidinophenyl)butanoyl]-L-seryl}-1,5,10-triazadecane and salt thereof.

5. 10-{N-[4-[4-guanidinophenyl]glycyl}-1,5,10-triazadecane and salt thereof.

* * * * *